(12) United States Patent
Takahashi et al.

(10) Patent No.: US 9,279,909 B2
(45) Date of Patent: *Mar. 8, 2016

(54) METHOD FOR POLARIZING A TERAHERTZ ELECTROMAGNETIC WAVE USING A POLARIZER

(71) Applicant: PANASONIC INTELLECTUAL PROPERTY MANAGEMENT CO., LTD., Osaka (JP)

(72) Inventors: Kohei Takahashi, Osaka (JP); Tsutomu Kanno, Kyoto (JP); Akihiro Sakai, Nara (JP); Yuka Yamada, Nara (JP)

(73) Assignee: PANASONIC INTELLECTUAL PROPERTY MANAGEMENT CO., LTD., Osaka (JP)

(*) Notice: Subject to any disclaimer, the term of this patent is extended or adjusted under 35 U.S.C. 154(b) by 29 days.

This patent is subject to a terminal disclaimer.

(21) Appl. No.: 14/043,719

(22) Filed: Oct. 1, 2013

(65) Prior Publication Data

US 2014/0029086 A1    Jan. 30, 2014

Related U.S. Application Data

(63) Continuation of application No. PCT/JP2013/000470, filed on Jan. 29, 2013.

(30) Foreign Application Priority Data

Feb. 1, 2012   (JP) ................... 2012-019476

(51) Int. Cl.
*G02B 5/30*   (2006.01)
*G02B 27/28*  (2006.01)
(Continued)

(52) U.S. Cl.
CPC ............ *G02B 1/08* (2013.01); *B29D 11/00644* (2013.01); *G02B 1/02* (2013.01); *G02B 5/3025* (2013.01); *G01N 21/3581* (2013.01)

(58) Field of Classification Search
CPC .. B29D 11/00644; G02B 5/30; G02B 5/3025; G02B 5/3083; G02B 1/02; G02B 1/08; G01N 21/3581; H01Q 15/24

USPC .......... 359/352, 489.01, 489.07, 489.15, 900; 501/86
See application file for complete search history.

(56) References Cited

U.S. PATENT DOCUMENTS

| 8,339,706 B2 | 12/2012 | Fujii et al. |
| 8,786,949 B2* | 7/2014 | Takahashi et al. ....... 359/489.07 |
| 2012/0015799 A1* | 1/2012 | Shonai ............................. 501/86 |
| 2013/0301128 A1* | 11/2013 | Takahashi et al. ....... 359/489.01 |

FOREIGN PATENT DOCUMENTS

| JP | 2009-052920 A | 3/2009 |
| JP | 2009-223010 A | 10/2009 |
| JP | 2010-256840 A | 11/2010 |

OTHER PUBLICATIONS

International Search Report issued in International Application No. PCT/JP2013I000470 with Date of mailing Mar. 5, (Continued)

*Primary Examiner* — Bumsuk Won
*Assistant Examiner* — Collin X Beatty
(74) *Attorney, Agent, or Firm* — McDermott Will & Emery LLP

(57) ABSTRACT

This disclosure provides a new method for polarizing an electromagnetic wave having a frequency of not less than 0.1 THz and not more than 0.8 THz using a polarizer. The method comprises: a step (a) of preparing the polarizer; wherein the polarizer comprises a sapphire single crystalline layer and a $Ca_xCoO_2$ crystalline layer, the $Ca_xCoO_2$ crystalline layer is stacked on the sapphire single crystalline layer, a surface of the $Ca_xCoO_2$ crystalline layer has a (010) surface orientation, and the $Ca_xCoO_2$ crystalline layer has a thickness of not less than 2 micrometers and not more than 20 micrometers; and a step (b) of irradiating the polarizer with the electromagnetic wave having a frequency of not less than 0.1 THz and not more than 0.8 THz to output an output wave having only a component parallel to a c-axis direction of the sapphire single crystalline layer.

10 Claims, 12 Drawing Sheets

(51) Int. Cl.
  *G02B 1/08* (2006.01)
  *B29D 11/00* (2006.01)
  *G02B 1/02* (2006.01)
  *G01N 21/3581* (2014.01)

(56) References Cited

OTHER PUBLICATIONS

Itsunari Yamada et al., "Terahertz wire-grid polarizers with micrometer-pitch Al gratings," Optics Letters, vol. 34, No. 3, pp. 274-276, 2009.

Lei Ren etal., "Carbon Nanotube Terahertz Polarizer," Nano Letters, vol. 9, No. 7, pp. 2610-2613, 2009.

Brian L. Cushing et al., "Topotactic Routes to Layered Calcium Cobalt Oxides," Journal of Solid State Chemistry, vol. 141, pp. 385-391, 1998.

H. X. Yang et al., "Structural properties and cation ordering in layered hexagonal CaxCoO2," Physical Review B., vol. 73, pp. 014109-6, 2006.

B. Cushing, et al., "Topotactic Routes to Layered Calcium Cobalt Oxides," Journal of Solid State Chemistry, vol. 141, pp. 385-391 (1998).

* cited by examiner

METHOD FOR POLARIZING A TERAHERTZ ELECTROMAGNETIC WAVE USING A POLARIZER

This application is a Continuation of PCT/JP2013/000470 filed on Jan. 29, 2013, which claims foreign priority of Japanese Patent Application No. 2012-019476 filed on Feb. 1, 2012, the entire contents of both of which are incorporated herein by reference.

BACKGROUND OF THE INVENTION

1. Field of the Invention

The present invention relates to a method for polarizing a terahertz electromagnetic wave using a polarizer.

2. Related Background Art

Terahertz electromagnetic wave is an electromagnetic wave having a frequency of 0.1 THz or more. JP 2009-052920 A, Itsunari Yamada et. al., "Terahertz wire-grid polarizers with micrometer-pitch Al gratings", Optics Letters, 2009, Vol. 34, No. 3, p.p. 274-276, and Lei Ren et. al., "Carbon Nanotube Terahertz Polarizer", Nano Letters, 2009, Vol. 9, No. 7, p.p. 2610-2613 disclose a method for polarizing a terahertz electromagnetic wave.

SUMMARY OF THE INVENTION

One non-limiting and exemplary embodiment provides a novel method for polarizing a terahertz electromagnetic wave using a polarizer.

Additional benefits and advantages of the disclosed embodiments will be apparent from the specification and Figures. The benefits and/or advantages may be individually provided by the various embodiments and features of the specification and drawings disclosure, and need not all be provided in order to obtain one or more of the same.

In one general aspect, the techniques disclosed here feature; a method for polarizing an electromagnetic wave having a frequency of not less than 0.1 THz and not more than 0.8 THz using a polarizer, the method comprising: a step (a) of preparing the polarizer; wherein the polarizer comprises a sapphire single crystalline layer, and a $Ca_xCoO_2$ crystalline layer, the $Ca_xCoO_2$ crystalline layer is stacked on the sapphire single crystalline layer, a surface of the $Ca_xCoO_2$ crystalline layer has a (010) surface orientation, and the $Ca_xCoO_2$ crystalline layer has a thickness of not less than 2 micrometers and not more than 20 micrometers; and a step (b) of irradiating the polarizer with the electromagnetic wave having a frequency of not less than 0.1 THz and not more than 0.8 THz to output an output wave having only a component parallel to a c-axis direction of the sapphire single crystalline layer.

These general and specific aspects may be implemented using a system, a method, and a computer program, and any combination of systems, methods, and computer programs.

DETAILED DESCRIPTION

Figure 1:
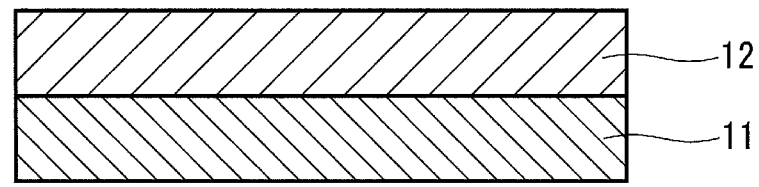
FIG. 1 shows a cross-sectional view of a terahertz polarizer of one embodiment.

The first embodiment provides a method for polarizing an electromagnetic wave having a frequency of not less than 0.1 THz and not more than 0.8 THz using a polarizer. The method comprises: a step (a) of preparing the polarizer; wherein the polarizer comprises a sapphire single crystalline layer, and a $Ca_xCoO_2$ crystalline layer, the $Ca_xCoO_2$ crystalline layer is stacked on the sapphire single crystalline layer, a surface of the $Ca_xCoO_2$ crystalline layer has a (010) surface orientation, and the $Ca_xCoO_2$ crystalline layer has a thickness of not less than 2 micrometers and not more than 20 micrometers; and a step (b) of irradiating the polarizer with the electromagnetic wave having a frequency of not less than 0.1 THz and not more than 0.8 THz to output an output wave having only a component parallel to a c-axis direction of the sapphire single crystalline layer.

The second embodiment provides, in addition to the first embodiment, the $Ca_xCoO_2$ crystalline layer has a thickness of not less than 2 micrometers and not more than 9 micrometers.

The third embodiment provides, in addition to the first embodiment, the $Ca_xCoO_2$ crystalline layer has a thickness of not less than 2 micrometers and not more than 4 micrometers.

The fourth embodiment provides, in addition to any one of the first to third embodiments, in the step (b), the sapphire single crystalline layer is irradiated with the electromagnetic wave and the $Ca_xCoO_2$ crystalline layer outputs the output wave.

The fifth embodiment provides, in addition to any one of the first to third embodiments, in the step (b), the $Ca_xCoO_2$ crystalline layer is irradiated with the electromagnetic wave and the sapphire single crystalline layer outputs the output wave.

The sixth embodiment provides, in addition to any one of the first to fifth embodiments, in the step (b), the polarizer is irradiated with the electromagnetic wave travelling along the vertical direction to the polarizer.

The seventh embodiment provides, in addition to any one of the first to sixth embodiments, in the step (b), the output wave is output from the polarizer along the vertical direction to the polarizer.

The eighth embodiment provides a polarizer comprising: a sapphire single crystalline layer, and a $Ca_xCoO_2$ crystalline layer, wherein the $Ca_xCoO_2$ crystalline layer is stacked on the sapphire single crystalline layer, a surface of the $Ca_xCoO_2$ crystalline layer has a (010) surface orientation, and the $Ca_xCoO_2$ crystalline layer has a thickness of not less than 2 micrometers and not more than 20 micrometers.

The ninth embodiment provides, in addition to the eighth embodiment, the $Ca_xCoO_2$ crystalline layer has a thickness of not less than 2 micrometers and not more than 9 micrometers.

The tenth embodiment provides, in addition to the eighth embodiment, the $Ca_xCoO_2$ crystalline layer has a thickness of not less than 2 micrometers and not more than 4 micrometers.

Embodiments of the present disclosure are described below with reference to figures.

(Embodiment)

FIG. 1 shows a cross-sectional view of a terahertz polarizer (hereinafter, referred to simply as "polarizer") according to one embodiment. The polarizer has a shape of a plate (plate-shaped). The polarizer includes a sapphire single crystalline layer 11, and a $Ca_xCoO_2$ crystalline layer 12. The $Ca_xCoO_2$ crystalline layer 12 is stacked on the sapphire single crystalline layer 11. It is desirable that no layer is interposed between the $Ca_xCoO_2$ crystalline layer 12 and the sapphire single crystalline layer 11.

Figure 2:
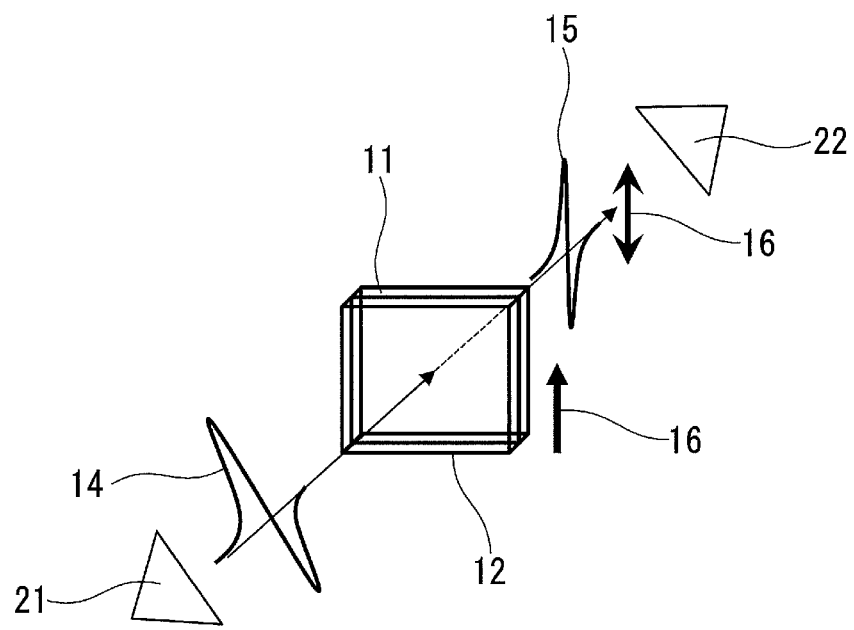
FIG. 2 schematically shows a method according to one embodiment.

FIG. 2 schematically shows a method for polarizing an electromagnetic wave using the polarizer according to one embodiment. The electromagnetic wave has a frequency of 0.1 THz or more and 0.8 THz or less. The polarizer is irradiated with the electromagnetic wave 14 that is an incident wave. An obverse face of the polarizer, which is the $Ca_xCoO_2$ crystalline layer 12 in the example of FIG. 2, is irradiated with the electromagnetic wave 14.

The electromagnetic wave that has passed through the polarizer is output from the polarizer as an output wave 15. The output wave 15 is output from a reverse face of the polarizer, which is the sapphire single crystalline layer 11 in the example of FIG. 2. The obverse face of the polarizer to which the incident wave enters may be the sapphire single crystalline layer 11, and the reverse face of the polarizer from which the output wave 15 is emitted may be the $Ca_xCoO_2$ crystalline layer 12. The output wave 15 has only a component parallel to the c-axis direction (see arrow 16 in FIG. 1) of the sapphire single crystalline layer 11. The output wave 15 does not have other components. An example of the other components is a component perpendicular to the c-axis direction of the sapphire single crystalline layer 11.

It is desirable that the sapphire single crystalline layer 11 has a (10-10) surface orientation, i.e. an m-plane orientation, on a surface thereof.

The surface of the $Ca_xCoO_2$ crystalline layer 12 has a (010) surface orientation. When this surface has a (001) surface orientation, the incident wave is not polarized, as demonstrated in Comparative Examples 5 to 15 described later.

The value of x is not limited as long as crystallinity of the $Ca_xCoO_2$ crystalline layer 12 is maintained. According to Brian. L. Cushing et al., "Topotactic Routes to Layered Calcium Cobalt Oxides", Journal of solid state chemistry, Vol. 141, pages 385-391 (1998), and H. X. Yang et al., "Structural Properties and Cation Ordering in Layered Hexagonal $Ca_xCoO_2$", Physical Review, B, Vol. 73, 014109-1 to 014109-6 (2006), the desirable value of x is 0.15 or more and 0.55 or less.

The $Ca_xCoO_2$ crystalline layer 12 has a thickness of not less than 2 micrometers and not more than 20 micrometers. When the thickness is less than 2 micrometers, the incident light is not sufficiently polarized, as demonstrated in Comparative Examples 1 and 2 described later. In other words, when the thickness is less than 2 micrometers, the component perpendicular to the c-axis direction of the sapphire single crystalline layer 11 is not removed sufficiently. On the other hand, when the thickness is more than 20 micrometers, it is difficult for the electromagnetic wave to pass through the polarizer, as demonstrated in Comparative Examples 3 and 4 described later. And thus, the output wave 15 having sufficient intensity is not obtained.

It is desirable that the $Ca_xCoO_2$ crystalline layer 12 has a thickness of not less than 2 micrometers and not more than 9 micrometers, as demonstrated in Examples 1 to 4. It is more desirable that the $Ca_xCoO_2$ crystalline layer 12 has a thickness of not less than 2 micrometers and not more than 4 micrometers, as demonstrated in Examples 1 and 2. This is because the component perpendicular to the c-axis direction of the sapphire single crystalline layer 11 is sufficiently removed, and the transmittance of the component parallel to the c-axis is high.

An angle formed between the obverse face of the polarizer and the incident wave is not limited. It is desirable that the incident wave enters into the polarizer with travelling along a vertical direction to the polarizer that has a shape of a plate.

EXAMPLES

The present disclosure can be understood in more detail by the following examples.

Example 1

(Fabrication of the Polarizer)

A $Ca_xCoO_2$ crystalline layer was formed by high frequency magnetron sputtering on a sapphire crystal substrate having a (10-10) surface orientation, i.e. an m-plane orientation, on the surface thereof. This sapphire crystal substrate was used as the sapphire single crystalline layer 11.

More specifically, a mixture target having a molar Ca:Co ratio of 1:1 was used in the high frequency magnetron sputtering.

First, gas in a film formation chamber was exhausted so that the internal pressure of the chamber has reached less than $1.0 \times 10^{-3}$ Pa.

Then, the sapphire single crystalline layer was heated by an heater while gas mixture of argon (volume ratio: 96%) and oxygen (volume ratio: 4%) was introduced into the chamber. Next, a $Ca_xCoO_2$ crystalline layer 12 having a thickness of 2 micrometers was formed on the sapphire single crystalline layer 11 by high frequency magnetron sputtering so as to form the $Ca_xCoO_2$ crystalline layer 12 having a (010) surface orientation on the surface thereof. A polarizer of Example 1 was thus obtained.

Conditions of the high frequency magnetron sputtering are described below.

Internal Pressure of the film formation chamber: 5 Pa
Temperature of the sapphire crystal substrate: 450 degrees Celsius
RF power: 100 W After the $Ca_xCoO_2$ crystalline layer 12 was formed, the polarizer was cooled to room temperature under pressure of 5 Pa for 60 minutes.

A composition ratio of cations included in the formed $Ca_xCoO_2$ crystalline layer 12 was measured using an energy dispersive X-ray analyzer. As a result, the composition ratio of Ca:Co was about 1:2, that is, the value of x was 0.5.

(Irradiation with the Incident Wave)

As shown in FIG. 2, the obtained polarizer was disposed between an electromagnetic wave emitting device 21 and an electromagnetic wave receiver 22.

The electromagnetic wave emitting device 21 was a dipole-type photoconductive antenna of a low-temperature-grown GaAs (available from HAMAMATSU Photonics K. K.). This photoconductive antenna was activated with a Ti:Sapphire laser.

The electromagnetic wave receiver 22 was a Bowtie-type photoconductive antenna of a low-temperature-grown GaAs (available from HAMAMATSU Photonics K. K.).

An electromagnetic wave was emitted from the electromagnetic wave emitting device 21 with varying its frequency from 0.1 THz to 0.8 THz.

The emitted electromagnetic wave was a pulsed wave polarized linearly.

The $Ca_xCoO_2$ crystalline layer 12, which was at an obverse face side of the polarizer, was irradiated with the electromagnetic wave with rotating the polarizer about a vertical direction to the polarizer as an rotation axis. The electromagnetic wave was controlled so that the wave travelled along the vertical direction and entered into the polarizer at each time of before and after the rotation. The rotation of the polarizer changed an inclination between the polarized wave and the c-axis of the sapphire single crystalline layer 11.

The electromagnetic wave was output as an output wave 15 from the sapphire single crystalline layer 11, which was at a reverse face side of the polarizer. The component of the light that is parallel to the c-axis direction of the sapphire single crystalline layer 11 was received by the electromagnetic wave receiver 22. This component was included in the output wave 15. Similarly, the component of the light which is perpendicular to the c-axis direction of the sapphire single crystalline layer 11 was received by the electromagnetic wave receiver 22.

Figure 5:
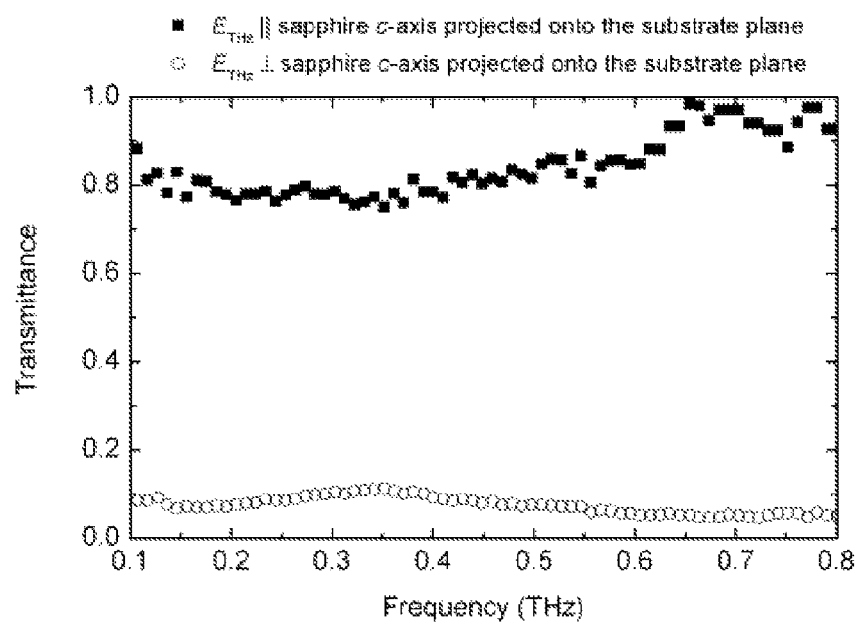
FIG. 5 shows a transmittance spectrum of a $Ca_xCoO_2$ crystalline layer (film thickness: 2 micrometers) having a surface orientation of (010), and formed on a sapphire single crystalline layer having an m-plane orientation on the surface thereof.

FIG. 5 shows the transmittance spectrum measured by the electromagnetic wave receiver 22 in Example 1.

In FIGS. 3 to 13, black squares indicate a transmittance of a component of light which is parallel to the c-axis direction of the sapphire single crystalline layer 11 having a (10-10) surface orientation (namely, an m-plane orientation) on the surface thereof. This is shown as "$E_{THz}$//the c-axis of the sapphire projected onto the substrate plane" in these figures. Also, in FIGS. 3 to 13, white circles indicate a transmittance of a component of light which is perpendicular to the c-axis direction of the sapphire single crystalline layer 11 having a (10-10) surface orientation (namely, an m-plane orientation) on the surface thereof. This is shown as ""$E_{THz} \perp$ the c-axis of the sapphire projected onto the substrate plane" in these figures.

The transmittance was calculated in accordance with the following formula: Transmittance=(Intensity of the output wave received by the electromagnetic wave receiver 22)/(Intensity of the electromagnetic wave emitted from the electromagnetic wave emitting device 21).

Example 2

Figure 6:
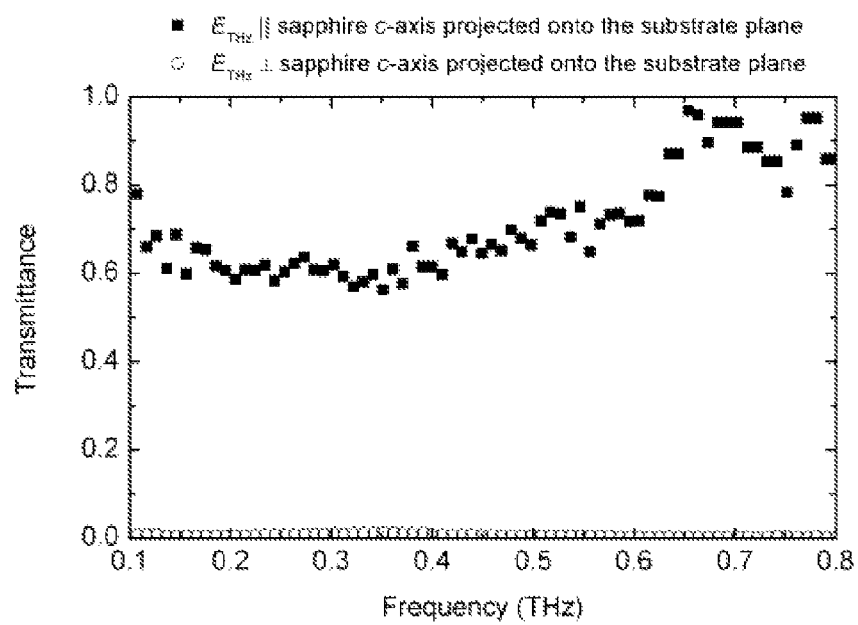
FIG. 6 shows a transmittance spectrum of a $Ca_xCoO_2$ crystalline layer (film thickness: 4 micrometers) having a surface orientation of (010), and formed on a sapphire single crystalline layer having an m-plane orientation on the surface thereof.

An experiment similar to Example 1 was performed except that the thickness of the $Ca_xCoO_2$ crystalline layer 12 was set at 4 micrometers. FIG. 6 shows the transmittance spectrum measured in Example 2.

Example 3

Figure 7:
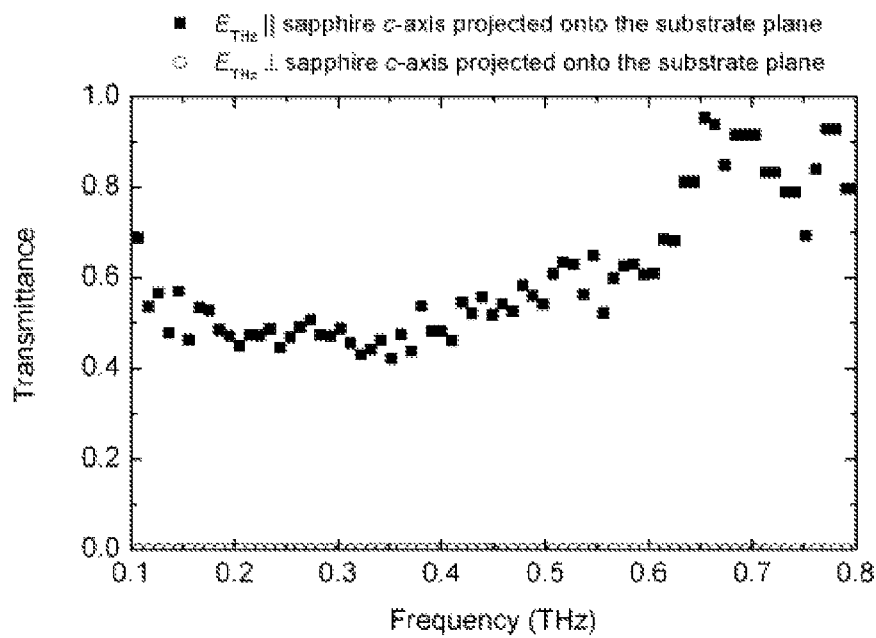
FIG. 7 shows a transmittance spectrum of a $Ca_xCoO_2$ crystalline layer (film thickness: 6 micrometers) having a surface orientation of (010), and formed on a sapphire single crystalline layer having an m-plane orientation on the surface thereof.

An experiment similar to Example 1 was performed except that the thickness of the $Ca_xCoO_2$ crystalline layer 12 was set at 6 micrometers. FIG. 7 shows the transmittance spectrum measured in Example 3.

Example 4

Figure 8:
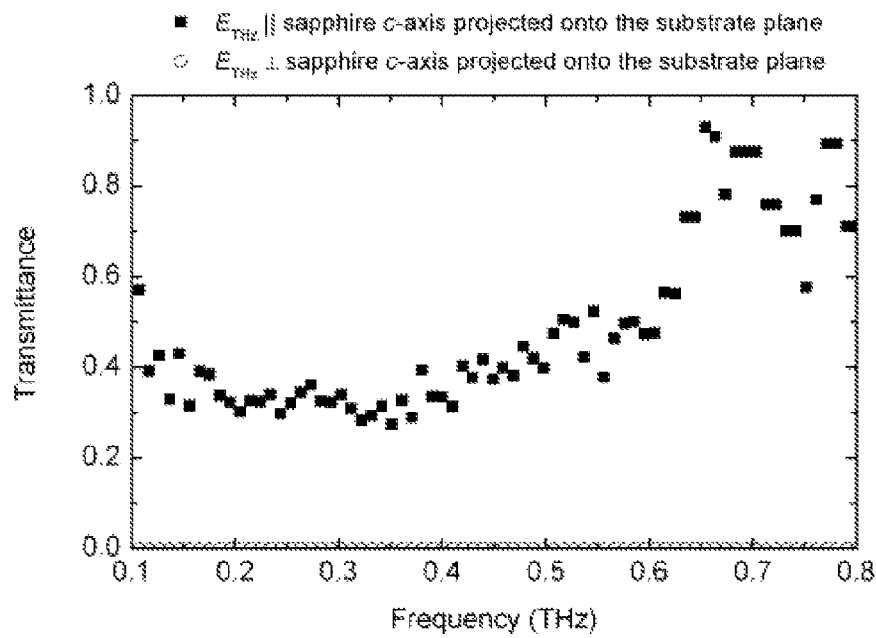
FIG. 8 shows a transmittance spectrum of a $Ca_xCoO_2$ crystalline layer (film thickness: 9 micrometers) having a surface orientation of (010), and formed on a sapphire single crystalline layer having an m-plane orientation on the surface thereof.

An experiment similar to Example 1 was performed except that the thickness of the $Ca_xCoO_2$ crystalline layer 12 was set at 9 micrometers. FIG. 8 shows the transmittance spectrum measured in Example 4.

Example 5

Figure 9:
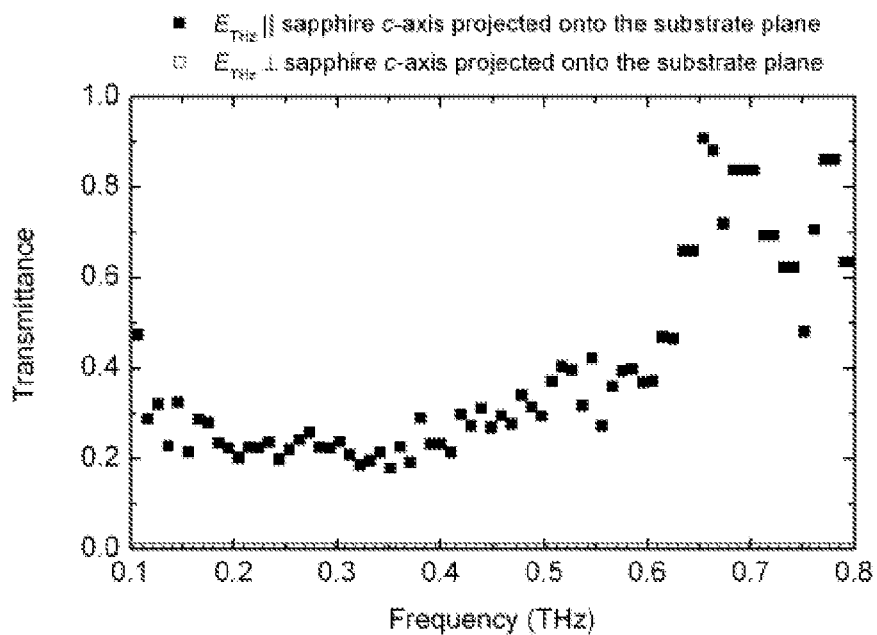
FIG. 9 shows a transmittance spectrum of a $Ca_xCoO_2$ crystalline layer (film thickness: 12 micrometers) having a surface orientation of (010), and formed on a sapphire single crystalline layer having an m-plane orientation on the surface thereof.

An experiment similar to Example 1 was performed except that the thickness of the $Ca_xCoO_2$ crystalline layer 12 was set at 12 micrometers. FIG. 9 shows the transmittance spectrum measured in Example 5.

Example 6

Figure 10:
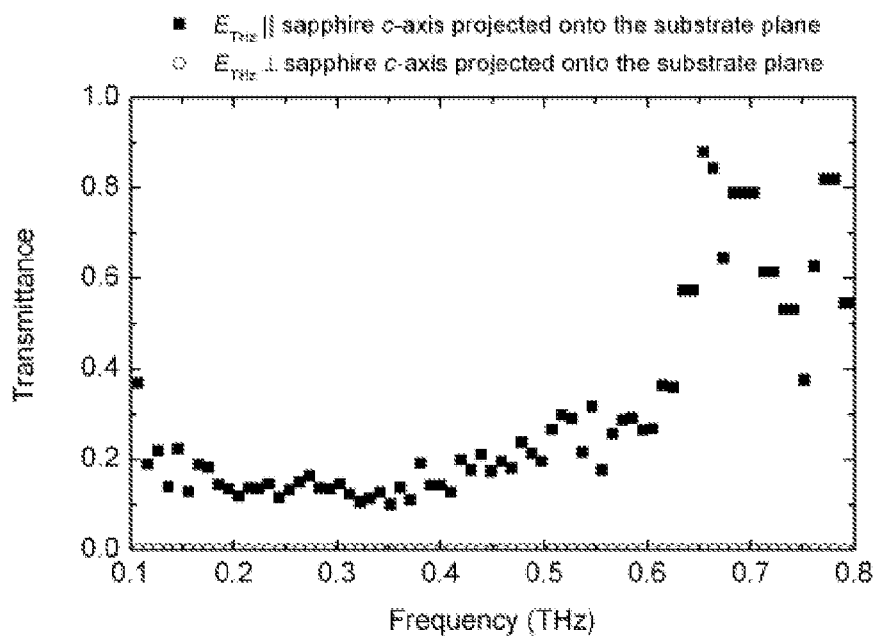
FIG. 10 shows a transmittance spectrum of a $Ca_xCoO_2$ crystalline layer (film thickness: 16 micrometers) having a surface orientation of (010), and formed on a sapphire single crystalline layer having an m-plane orientation on the surface thereof.

An experiment similar to Example 1 was performed except that the thickness of the $Ca_xCoO_2$ crystalline layer 12 was set at 16 micrometers. FIG. 10 shows the transmittance spectrum measured in Example 6.

Example 7

Figure 11:
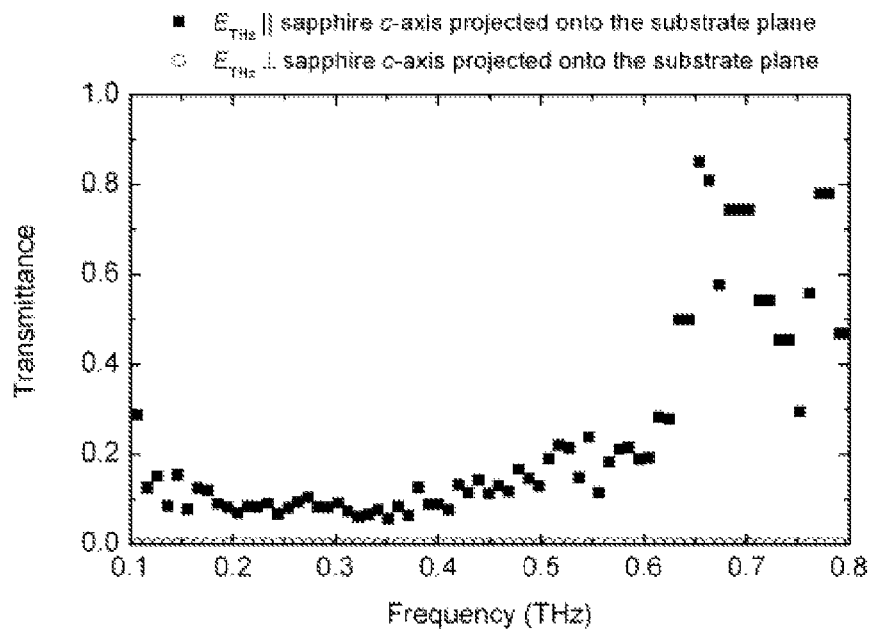
FIG. 11 shows a transmittance spectrum of a $Ca_xCoO_2$ crystalline layer (film thickness: 20 micrometers) having a surface orientation of (010), and formed on a sapphire single crystalline layer having an m-plane orientation on the surface thereof.

An experiment similar to Example 1 was performed except that the thickness of the $Ca_xCoO_2$ crystalline layer 12 was set at 20 micrometers. FIG. 11 shows the transmittance spectrum measured in Example 7.

Comparative Example 1

Figure 3:
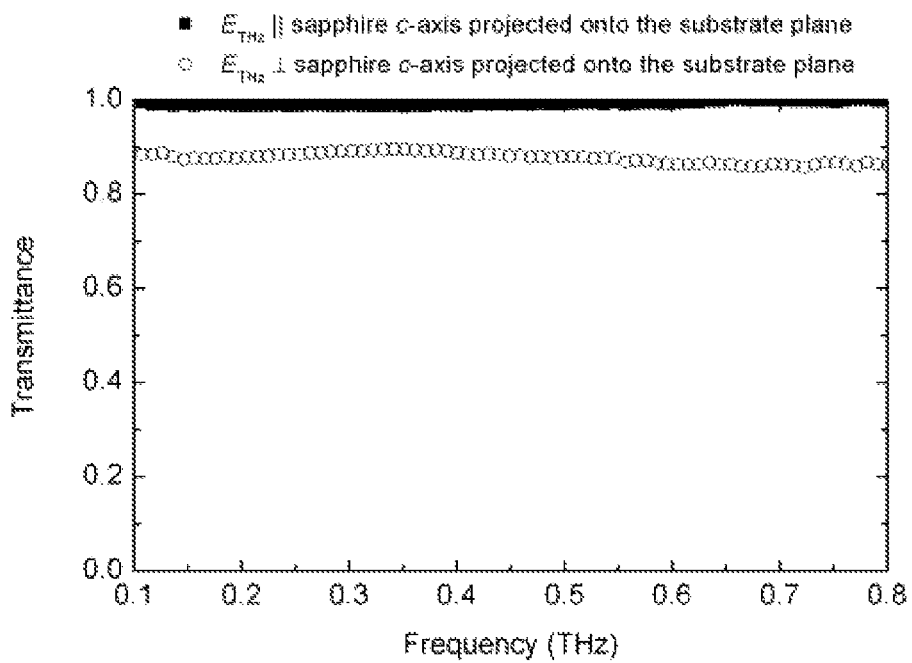
FIG. 3 shows a transmittance spectrum of a $Ca_xCoO_2$ crystalline layer (film thickness: 0.1 micrometer) having a surface orientation of (010), and formed on a sapphire single crystalline layer having an m-plane orientation on the surface thereof.

An experiment similar to Example 1 was performed except that the thickness of the $Ca_xCoO_2$ crystalline layer 12 was set at 0.1 micrometer. FIG. 3 shows the transmittance spectrum measured in Comparative Example 1.

Comparative Example 2

Figure 4:
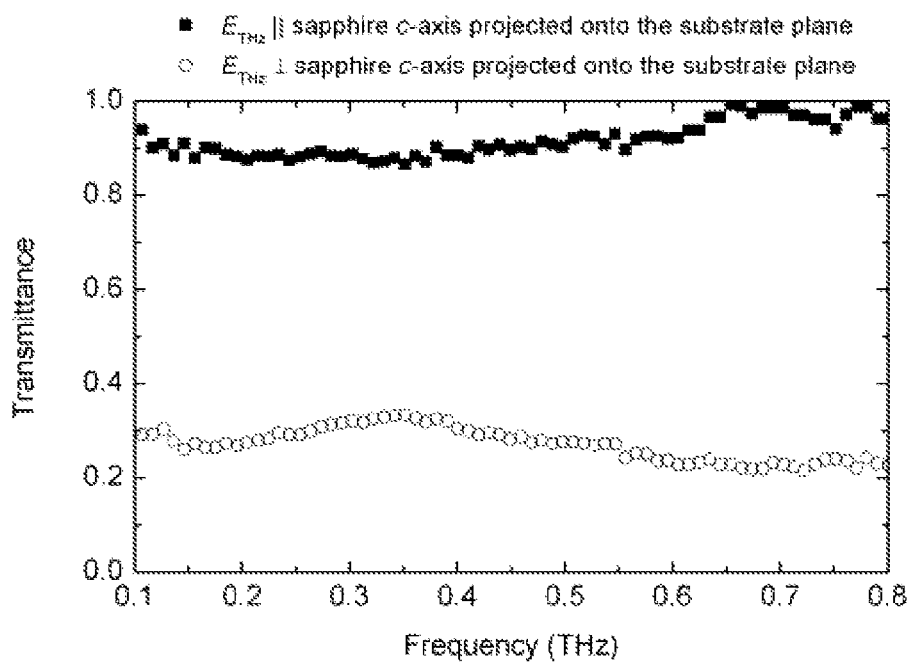
FIG. 4 shows a transmittance spectrum of a $Ca_xCoO_2$ crystalline layer (film thickness: 1 micrometer) having a surface orientation of (010), and formed on a sapphire single crystalline layer having an m-plane orientation on the surface thereof.

An experiment similar to Example 1 was performed except that the thickness of the $Ca_xCoO_2$ crystalline layer 12 was set at 1 micrometer. FIG. 4 shows the transmittance spectrum measured in Comparative Example 2.

Comparative Example 3

Figure 12:
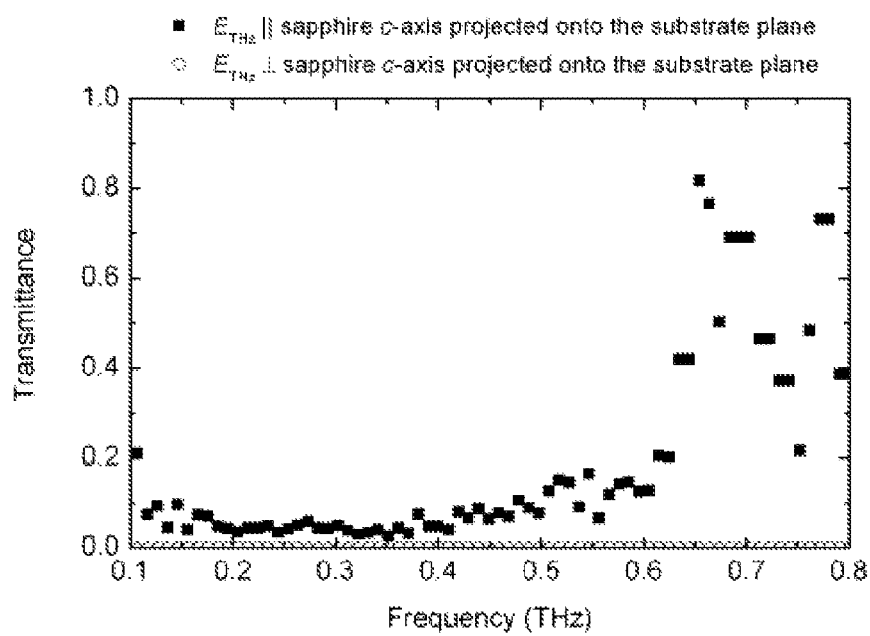
FIG. 12 shows a transmittance spectrum of a $Ca_xCoO_2$ crystalline layer (film thickness: 25 micrometers) having a surface orientation of (010), and formed on a sapphire single crystalline layer having an m-plane orientation on the surface thereof.

An experiment similar to Example 1 was performed except that the thickness of the $Ca_xCoO_2$ crystalline layer 12 was set at 25 micrometers. FIG. 12 shows the transmittance spectrum measured in Comparative Example 3.

Comparative Example 4

Figure 13:
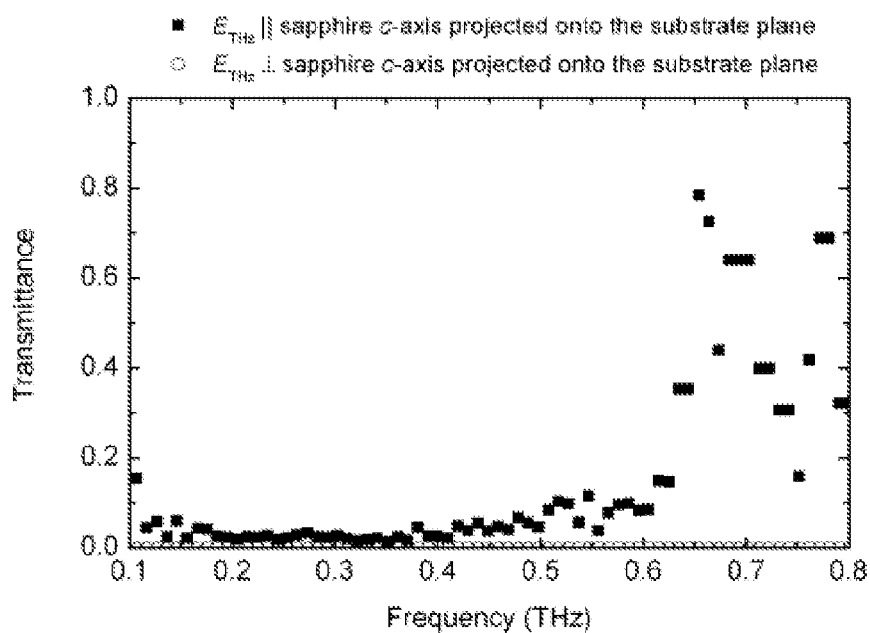
FIG. 13 shows a transmittance spectrum of a $Ca_xCoO_2$ crystalline layer (film thickness: 30 micrometers) having a surface orientation of (010), and formed on a sapphire single crystalline layer having an m-plane orientation on the surface thereof.
Figure 14:
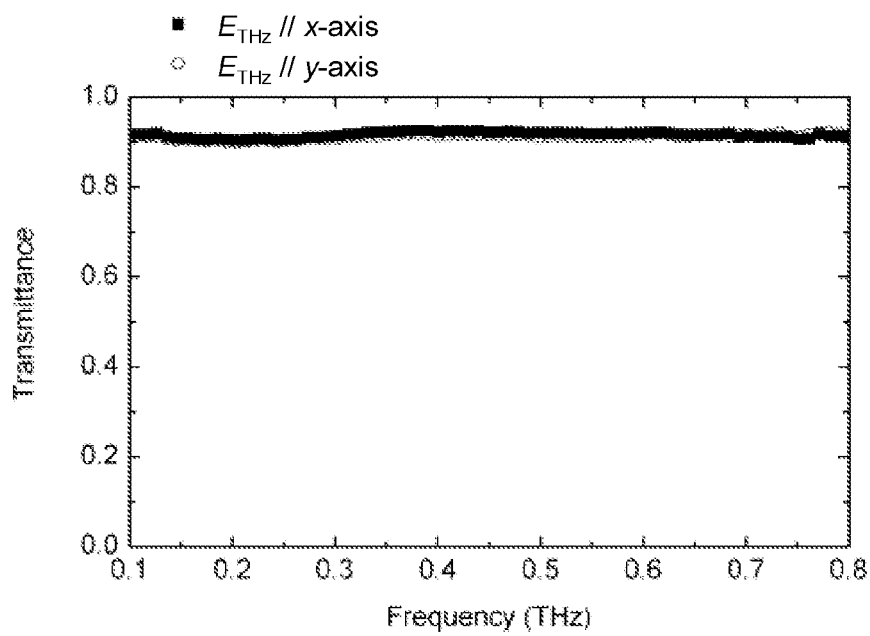
FIG. 14 shows a transmittance spectrum of a $Ca_xCoO_2$ crystalline layer (film thickness: 0.1 micrometer) having a surface orientation of (010), and formed on a sapphire single crystalline layer having a c-plane orientation on the surface thereof.
Figure 15:
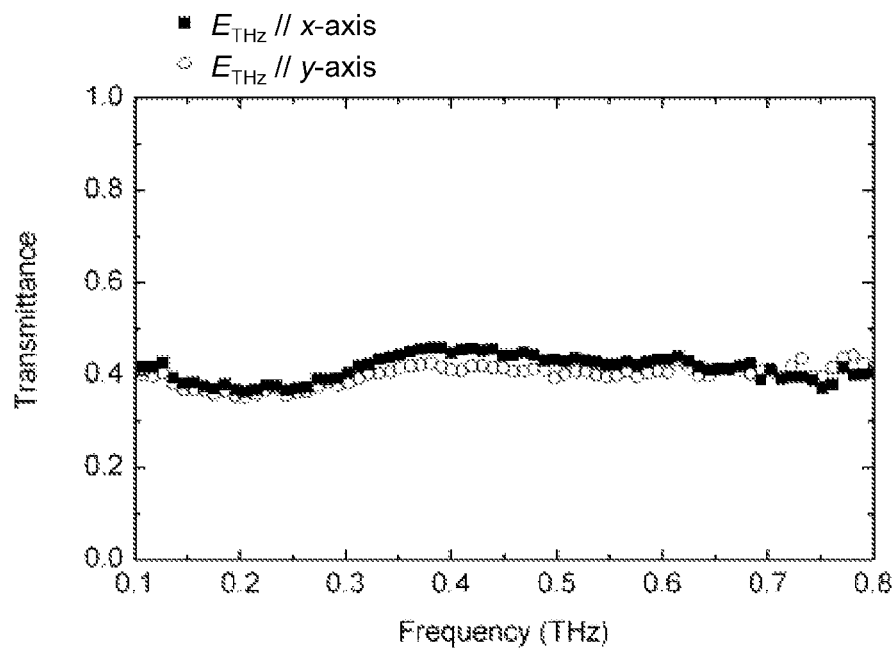
FIG. 15 shows a transmittance spectrum of a $Ca_xCoO_2$ crystalline layer (film thickness: 1 micrometer) having a surface orientation of (010), and formed on a sapphire single crystalline layer having a c-plane orientation on the surface thereof.
Figure 16:
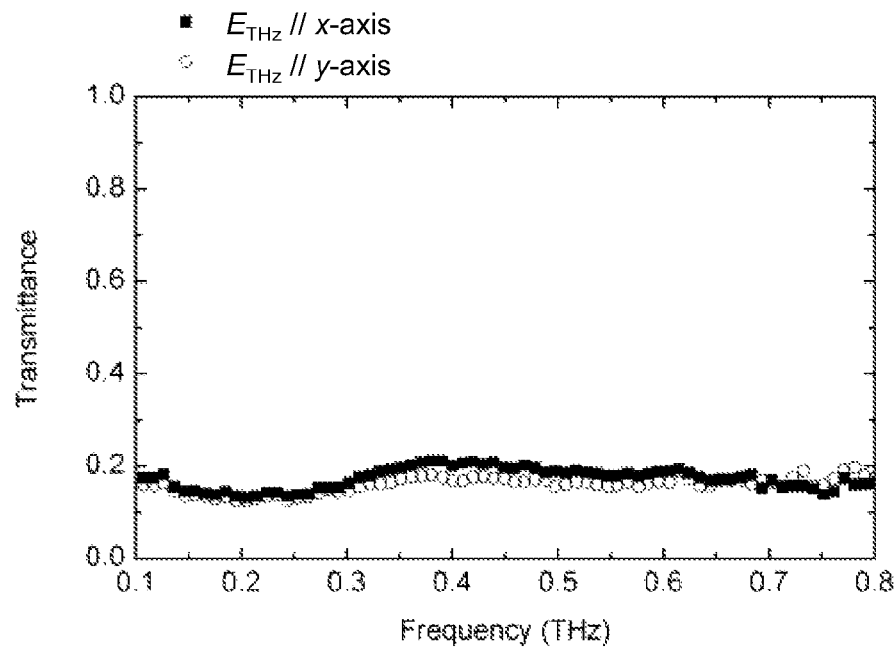
FIG. 16 shows a transmittance spectrum of a $Ca_xCoO_2$ crystalline layer (film thickness: 2 micrometers) having a surface orientation of (010), and formed on a sapphire single crystalline layer having a c-plane orientation on the surface thereof.
Figure 17:
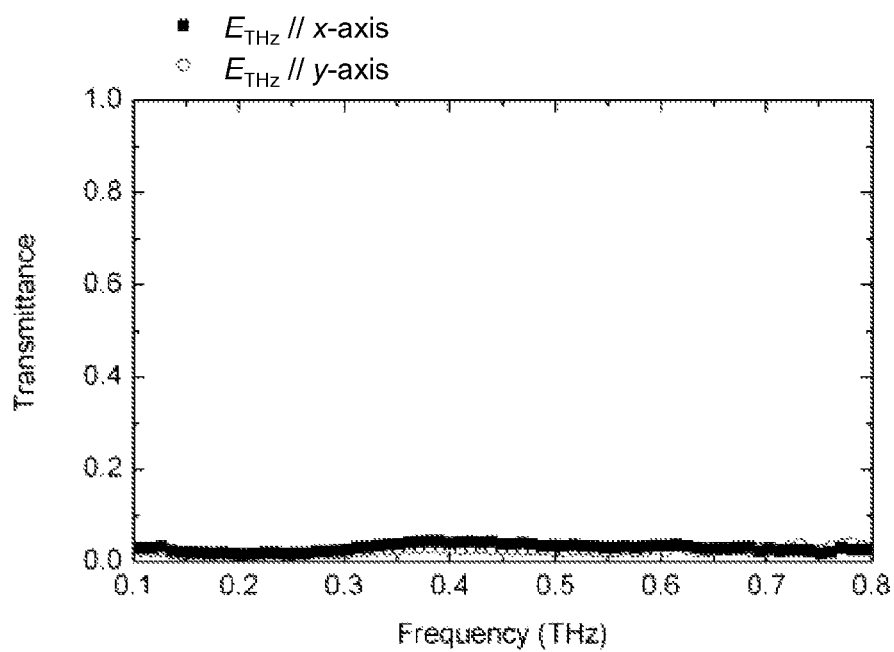
FIG. 17 shows a transmittance spectrum of a $Ca_xCoO_2$ crystalline layer (film thickness: 4 micrometers) having a surface orientation of (010), and formed on a sapphire single crystalline layer having a c-plane orientation on the surface thereof.
Figure 18:
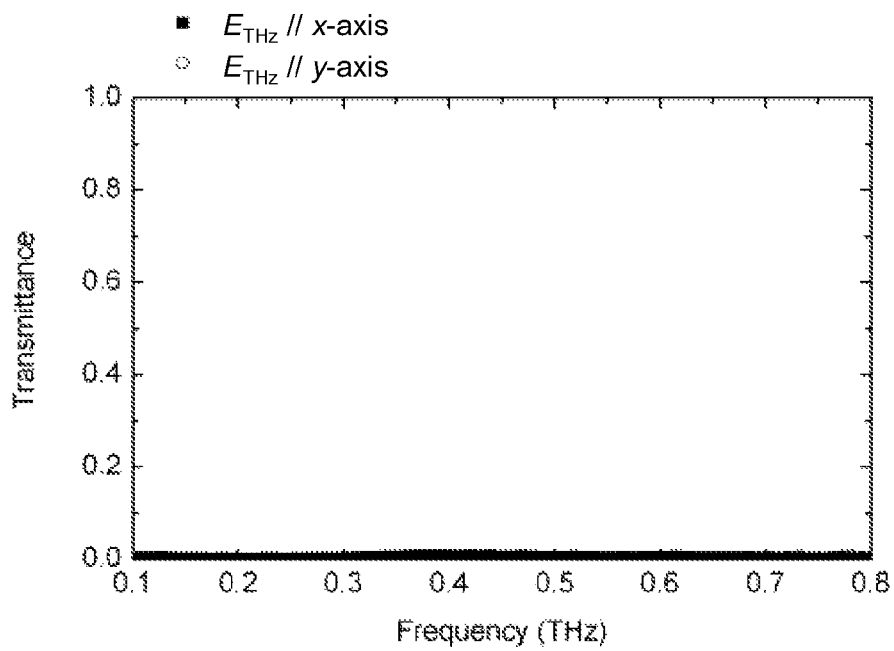
FIG. 18 shows a transmittance spectrum of a $Ca_xCoO_2$ crystalline layer (film thickness: 6 micrometers) having a surface orientation of (010), and formed on a sapphire single crystalline layer having a c-plane orientation on the surface thereof.
Figure 19:
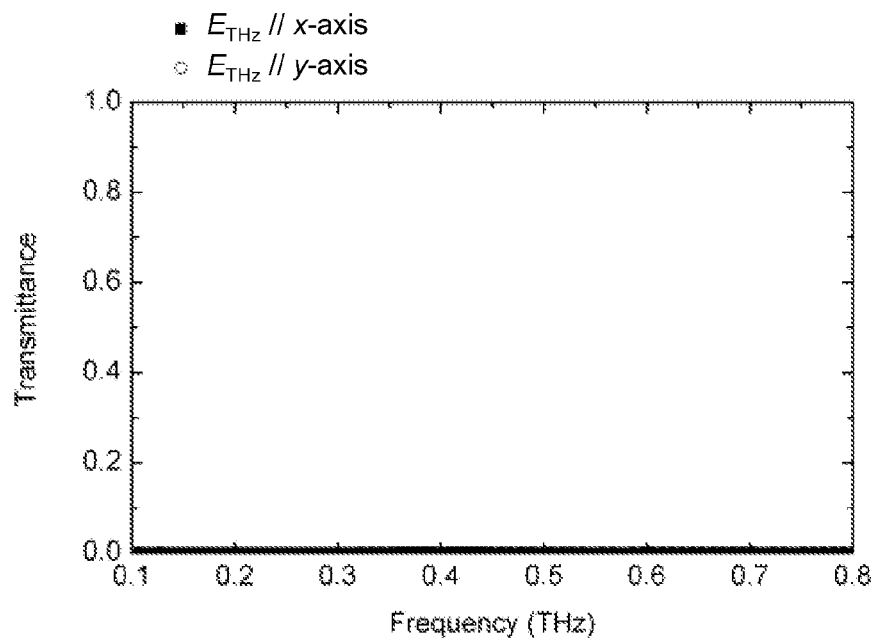
FIG. 19 shows a transmittance spectrum of a $Ca_xCoO_2$ crystalline layer (film thickness: 9 micrometers) having a surface orientation of (010), and formed on a sapphire single crystalline layer having a c-plane orientation on the surface thereof.
Figure 20:
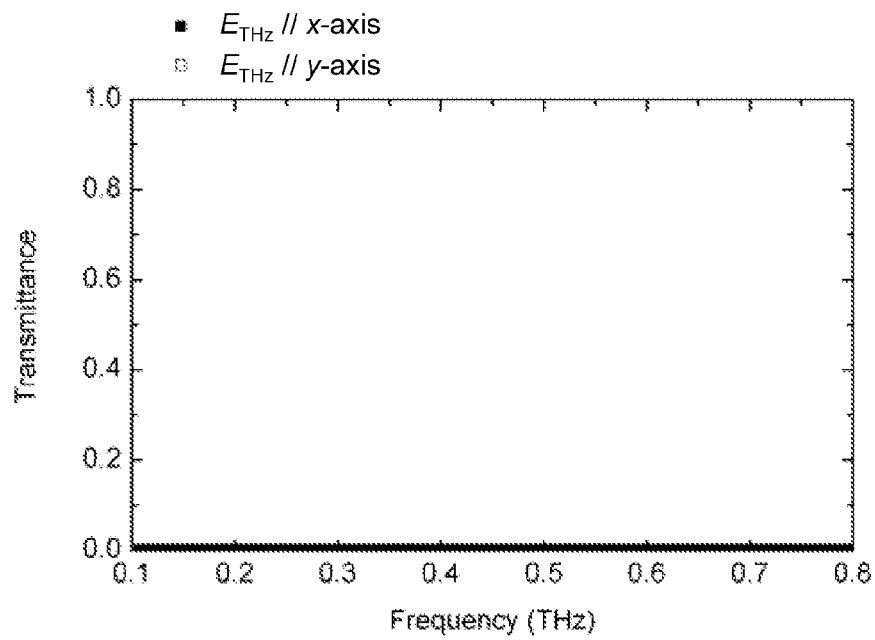
FIG. 20 shows a transmittance spectrum of a $Ca_xCoO_2$ crystalline layer (film thickness: 12 micrometers) having a surface orientation of (010), and formed on a sapphire single crystalline layer having a c-plane orientation on the surface thereof.
Figure 21:
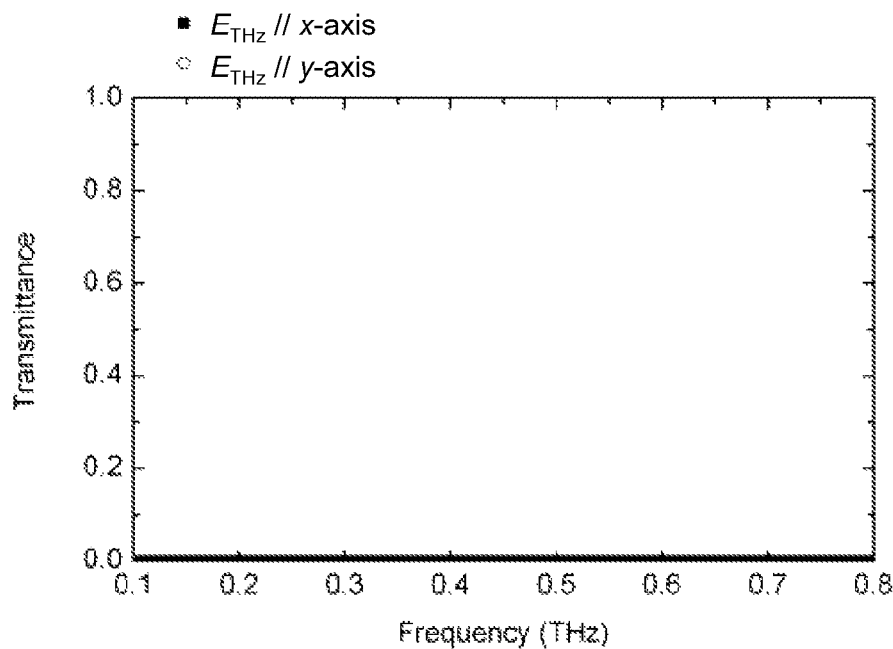
FIG. 21 shows a transmittance spectrum of a $Ca_xCoO_2$ crystalline layer (film thickness: 16 micrometers) having a surface orientation of (010), and formed on a sapphire single crystalline layer having a c-plane orientation on the surface thereof.
Figure 22:
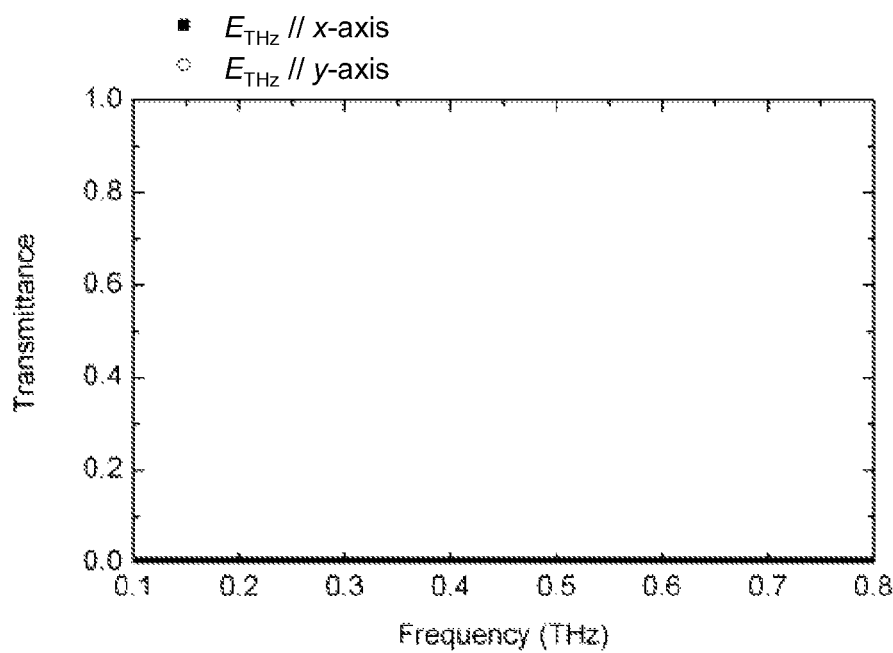
FIG. 22 shows a transmittance spectrum of a $Ca_xCoO_2$ crystalline layer (film thickness: 20 micrometers) having a surface orientation of (010), and formed on a sapphire single crystalline layer having a c-plane orientation on the surface thereof.
Figure 23:
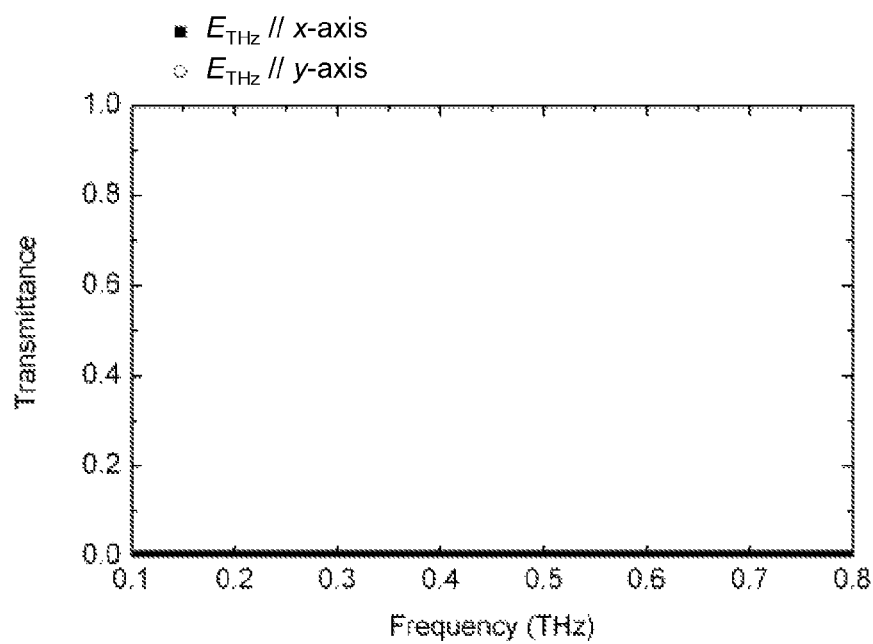
FIG. 23 shows a transmittance spectrum of a $Ca_xCoO_2$ crystalline layer (film thickness: 25 micrometers) having a surface orientation of (010), and formed on a sapphire single crystalline layer having a c-plane orientation on the surface thereof.
Figure 24:
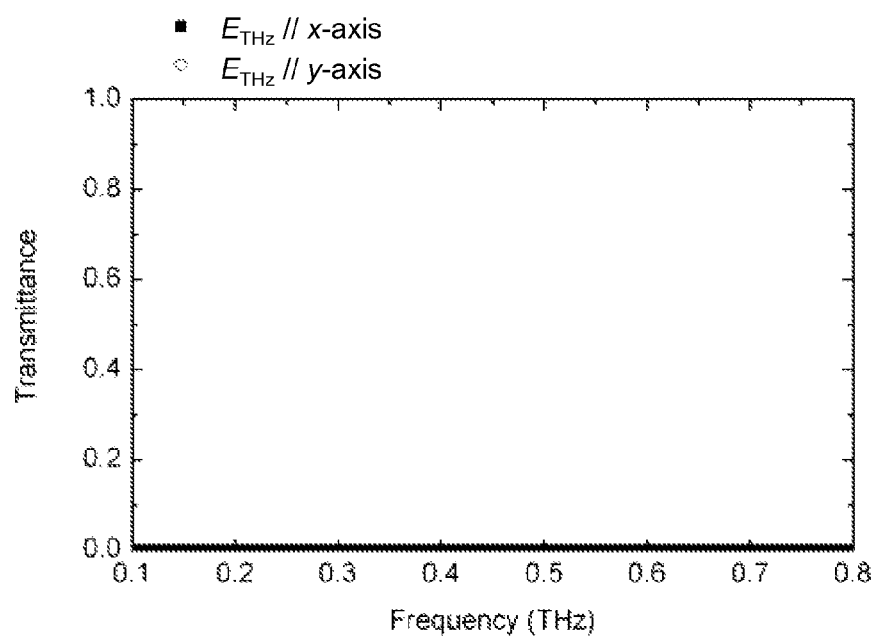
FIG. 24 shows a transmittance spectrum of a $Ca_xCoO_2$ crystalline layer (film thickness: 30 micrometers) having a surface orientation of (010), and formed on a sapphire single crystalline layer having a c-plane orientation on the surface thereof.

An experiment similar to Example 1 was performed except that the thickness of the $Ca_xCoO_2$ crystalline layer 12 was set at 30 micrometers. FIG. 13 shows the transmittance spectrum measured in Comparative Example 4

The following Table 1 collectively shows average transmittances of Examples 1 to 7 and Comparative Examples 1 to 4. In Table 1, "Average transmittance parallel to c-axis" means an average value of the transmittance of the component parallel to the c-axis direction of the sapphire single crystalline layer 11. Also, "Average transmittance perpendicular to c-axis" means an average value of the transmittance of the component perpendicular to the c-axis direction of the sapphire single crystalline layer 11.

TABLE 1

| | Thickness of $Ca_xCoO_2$ layer 12 (µm) | Average transmittance parallel to c - axis | Average transmittance perpendicular to c - axis | Figure |
|---|---|---|---|---|
| Comp. Ex. 1 | 0.1 | 0.99 | 0.88 | FIG. 3 |
| Comp. Ex. 2 | 1 | 0.92 | 0.27 | FIG. 4 |
| Example 1 | 2 | 0.84 | 0.07 | FIG. 5 |
| Example 2 | 4 | 0.71 | 0.01 | FIG. 6 |
| Example 3 | 6 | 0.61 | 0.00 | FIG. 7 |
| Example 4 | 9 | 0.49 | 0.00 | FIG. 8 |
| Example 5 | 12 | 0.40 | 0.00 | FIG. 9 |
| Example 6 | 16 | 0.31 | 0.00 | FIG. 10 |
| Example 7 | 20 | 0.25 | 0.00 | FIG. 11 |
| Comp. Ex. 3 | 25 | 0.19 | 0.00 | FIG. 12 |
| Comp. Ex. 4 | 30 | 0.16 | 0.00 | FIG. 13 |

As is clear from Table 1, when the $Ca_xCoO_2$ crystalline layer 12 had a thickness of not less than 2 micrometers and not more than 20 micrometers, the average transmittance parallel to c-axis was not less than 0.25 and the average transmittance perpendicular to c-axis was not more than 0.07.

This means that the output wave 15 substantially included only a component parallel to the c-axis direction of the sapphire single crystalline layer 11. In other words, a component perpendicular to the c-axis direction of the sapphire single crystalline layer 11 was sufficiently removed.

It is desirable that the $Ca_xCoO_2$ crystalline layer 12 has a thickness of not less than 2 micrometers and not more than 9 micrometers, in order to increase the average transmittance parallel to the c-axis. It is more desirable that the $Ca_xCoO_2$ crystalline layer 12 has a thickness of not less than 2 micrometers and not more than 4 micrometers.

When the $Ca_xCoO_2$ crystalline layer 12 had a thickness of not more than 1 micrometer, the component perpendicular to the c-axis direction of the sapphire single crystalline layer 11 was not sufficiently removed.

When the $Ca_xCoO_2$ crystalline layer 12 had a thickness of more than 20 micrometers, not only the average transmittance perpendicular to the c-axis but also that parallel to the c-axis were decreased.

Comparative Examples 5 to 15

In Comparative Examples 5 to 15, experiments similar to Examples 1 to 7 and Comparative Examples 1 to 4 were conducted except that the $Ca_xCoO_2$ crystalline layer 12 having a (001) surface orientation (namely, a c-plane orientation) on the surface thereof was formed. To form this layer 12, a sapphire crystalline substrate having a (0001) surface orientation (namely, a c-plane orientation) on the surface thereof was used instead of the sapphire substrate having a (10-10) surface orientation (namely, an m-plane orientation) on the surface thereof.

In FIGS. 14 to 24, black squares indicate a transmittance of a component of light which is parallel to the x-axis direction of the sapphire single crystalline layer 11 having a (0001) surface orientation (namely, a c-plane orientation) on the surface thereof. This is shown as "$E_{THz}$//x-axis" in these figures. Also, in FIGS. 14 to 24, white circles indicate a transmittance of a components of light which is parallel to the y-axis direction of the sapphire single crystalline layer 11 having a (0001) surface orientation (namely, a c-plane orientation) on the surface thereof. This is shown as ""$E_{THz}$//the y-axis" in these figures. The x-axis and the y-axis are an arbitrary axis on the c-plane of the sapphire single crystalline layer 11 (a sapphire crystal does not have anisotropy in the c-plane). Note that the x-axis direction is perpendicular to the y-axis direction. Table 2 shows the results of Comparative Examples 5 to 15.

TABLE 2

|  | Thickness of $Ca_xCoO_2$ layer12 (μm) | Average transmittance parallel to x - axis | Average transmittance parallel to y - axis | Figure |
|---|---|---|---|---|
| Comp. Ex. 12 | 0.1 | 0.92 | 0.91 | FIG. 14 |
| Comp. Ex. 13 | 1 | 0.41 | 0.40 | FIG. 15 |
| Comp. Ex. 5 | 2 | 0.17 | 0.16 | FIG. 16 |
| Comp. Ex. 6 | 4 | 0.03 | 0.03 | FIG. 17 |
| Comp. Ex. 7 | 6 | 0.01 | 0.00 | FIG. 18 |
| Comp. Ex. 8 | 9 | 0.00 | 0.00 | FIG. 19 |
| Comp. Ex. 9 | 12 | 0.00 | 0.00 | FIG. 20 |
| Comp. Ex. 10 | 16 | 0.00 | 0.00 | FIG. 21 |
| Comp. Ex. 11 | 20 | 0.00 | 0.00 | FIG. 22 |
| Comp. Ex. 14 | 25 | 0.00 | 0.00 | FIG. 23 |
| Comp. Ex. 15 | 30 | 0.00 | 0.00 | FIG. 24 |

As is clear from table 2, the output wave 15 included both of the component parallel to the x-axis direction of the sapphire single crystalline layer 11 and the component parallel to the y-axis direction of the sapphire single crystalline layer 11, on almost the same level of transmittance (see Comparative Examples 5, 6, 12, and 13). This means that the incident wave was not polarized at all.

In Comparative examples 7-11, 14 and 15, the output wave 15 itself was not measured. This is because the $Ca_xCoO_2$ layer 12 was too thick.

The polarizer of the present disclosure can be used in, for example, an optical device, a medical equipment, or a security device.

The invention may be embodied in other forms without departing from the spirit or essential characteristics thereof. The embodiments disclosed in this application are to be considered in all respects as illustrative and not limiting. The scope of the invention is indicated by the appended claims rather than by the foregoing description, and all changes which come within the meaning and range of equivalency of the claims are intended to be embraced therein.

What is claimed is:

1. A method for polarizing an electromagnetic wave having a frequency of not less than 0.1 THz and not more than 0.8 THz using a polarizer, the method comprising:
   a step (a) of preparing the polarizer; wherein
      the polarizer comprises a sapphire single crystalline layer, and a $Ca_xCoO_2$ crystalline layer,
      the $Ca_xCoO_2$ crystalline layer is stacked on the sapphire single crystalline layer,
      a surface of the $Ca_xCoO_2$ crystalline layer has a (010) surface orientation, and
      the $Ca_xCoO_2$ crystalline layer has a thickness of not less than 2 micrometers and not more than 20 micrometers; and
   a step (b) of irradiating the polarizer with the electromagnetic wave having a frequency of not less than 0.1 THz and not more than 0.8 THz to output an output wave having only a component parallel to a c-axis direction of the sapphire single crystalline layer.

2. The method according to claim 1, wherein the $Ca_xCoO_2$ crystalline layer has a thickness of not less than 2 micrometers and not more than 9 micrometers.

3. The method according to claim 1, wherein the $Ca_xCoO_2$ crystalline layer has a thickness of not less than 2 micrometers and not more than 4 micrometers.

4. The method according to claim 1, wherein in the step (b), the sapphire single crystalline layer is irradiated with the electromagnetic wave and the $Ca_xCoO_2$ crystalline layer outputs the output wave.

5. The method according to claim 1, wherein in the step (b), the $Ca_xCoO_2$ crystalline layer is irradiated with the electromagnetic wave and the sapphire single crystalline layer outputs the output wave.

6. The method according to claim 1, wherein in the step (b), the polarizer is irradiated with the electromagnetic wave travelling along the vertical direction to the polarizer.

7. The method according to claim 6, wherein in the step (b), the output wave is output from the polarizer along the vertical direction to the polarizer.

8. A polarizer comprising:
   a sapphire single crystalline layer; and
   a $Ca_xCoO_2$ crystalline layer; wherein
   the $Ca_xCoO_2$ crystalline layer is stacked on the sapphire single crystalline layer,
   a surface of the $Ca_xCoO_2$ crystalline layer has a (010) surface orientation, and
   the $Ca_xCoO_2$ crystalline layer has a thickness of not less than 2 micrometers and not more than 20 micrometers.

9. The polarizer according to claim 8, wherein the $Ca_xCoO_2$ crystalline layer has a thickness of not less than 2 micrometers and not more than 9 micrometers.

10. The polarizer according to claim 8, wherein the $Ca_xCoO_2$ crystalline layer has a thickness of not less than 2 micrometers and not more than 4 micrometers.

* * * * *